United States Patent [19]

Kukla

[11] Patent Number: 4,742,068
[45] Date of Patent: May 3, 1988

[54] DIHYDROPYRIDINE COMPOUNDS HAVING 1,4,4-TRISUBSTITUTION USEFUL AS ANTIHYPERTENSIVE AGENTS

[75] Inventor: Michael J. Kukla, Maple Glen, Pa.

[73] Assignee: McNeilab, Inc., Fort Washington, Pa.

[21] Appl. No.: 871,943

[22] Filed: Jun. 9, 1986

[51] Int. Cl.$^4$ .................. C07D 211/82; A61K 31/44
[52] U.S. Cl. .................. 514/354; 514/278;
514/277; 514/332; 514/357; 546/328; 546/323;
546/314; 546/329; 546/341; 546/342; 546/262;
546/280; 546/275; 546/276; 546/281; 546/16;
544/238; 544/333; 544/360
[58] Field of Search ............ 546/323, 329, 341, 342,
546/328, 314; 514/354, 357

[56] References Cited

FOREIGN PATENT DOCUMENTS 545639 3/1977 U.S.S.R. .
568641 11/1977 U.S.S.R. .

OTHER PUBLICATIONS

Hesse et al., CA 98(9) 71252t.
Naito et al., CA 94:192101a.
Eckert-Maksic et al., CA 105:42176d.
Fraenkel et al., CA 105:78243n.
Tetrahedron Letters, No. 16, "N-Acyl-1,4-Dihydropyridines..." Joseph S. Foos et al., pp. 1407–1410, 1978.
J. Org. Chem. "Synthesis and Nuclear Magnetic Resonance..." Joseph Foos et al., vol. 44, No. 14, pp. 2522–2529, 1979.
Comptes. Rendus. Acad. Bu. Sci., "Preparation of β,βDiphenylglutaric Acid and its Derivatives", H. Ivanov et al., 18(6) 1965.
Indian Journal of Chemistry, "Decarboxylative Cleavage During Friedel-Crafts Reaction...", U. V. Korgaonkar et al., vol. 20B, pp. 572–574, Jul. 1981.
Tetrahedron Letters, No. 4, "2-Amino-1,2,3,4-Tetrahydropyridines", G. Fraenkel et al., pp. 327–330, 1978.
Synthesis, "Dihydropyridines; V*. Synthesis of 4,4-Disubstituted 1,4-Dihydropyridines...", Lutz-F. Tietze et al., pp. 190–192, Mar. 1986.
J. Am. Chem. Soc., "Generation of a Stable Spiro Dihydroaromatic Anion", vol. 94, No. 13, pp. 4732–4734, Jun. 28, 1972, Fraenkel et al.
J. Am. Chem. Soc, "Generation of Spirodihydroaromatic Anions, Chemistry and $^{13}$C NMR", S.O.A. Rizvi et al., vol. 101, No. 16, pp. 4488–4492, Aug. 1, 1979.
J. of Chem., "The Synthesis and Properties of Some Simple 1,4-Dihydropyridines", E. M. Kosower et al., vol. 27, pp. 3764–3771 (1962).
Spektroskopische und elektrochemische Eigenschaften N-Substituierter 1,4-Dihydro-4,4-dimethylpyridine, Liebigs Ann. Chem. Hesse et al., (1982), pp. 2079–2086.

Primary Examiner—Jane T. Fan
Attorney, Agent, or Firm—David J. Levy

[57] ABSTRACT

Dihydropyridine compounds having 1,4,4-trisubstitution of the following formula (I):

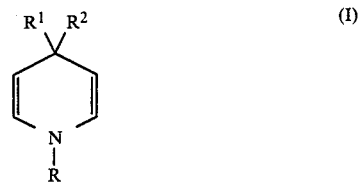

wherein
R is one of —COR$^3$, R$^3$ being a group such as phenyl or benzyl; R$^4$ where R$^4$ is a heterocycle; —(CH$_2$)$_n$NR$^5$R$^6$, with R$^5$ and R$^6$ being alkyl or joined to define a ring; or —(CH$_2$)$_n$COOR$^7$, with R$^7$ being alkyl or benzyl.

R$^1$ and R$^2$ are alkyl, phenyl or substituted phenyl.

The compounds are useful for the treatment of hypertension in mammals, e.g., in humans.

13 Claims, No Drawings

DIHYDROPYRIDINE COMPOUNDS HAVING 1,4,4-TRISUBSTITUTION USEFUL AS ANTIHYPERTENSIVE AGENTS

The present invention comprises various 1,4,4-trisubstituted dihydropyridine compounds which are useful in the treatment of hypertension in mammals, e.g. in humans.

N-Benzoyl-4,4-dimethyl-1,4-dihydropyridine is a known compound that is disclosed by Joseph S. Foos et al. in Tetrahedron Letters No. 16, page 1407 (1978).

SUMMARY OF THE INVENTION

Dihydropyridine compounds having 1,4,4-trisubstitution of the following formula (I):

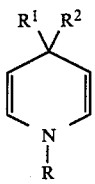
(I)

wherein R, $R^1$ and $R^2$ are as defined herein have antihypertensive properties when administered to a mammal in need thereof. Also part of the invention are pharmaceutical compositions containing compounds of the formula (I) and methods of treatment using such compositions.

DETAILED DESCRIPTION OF THE INVENTION

Compounds of the invention are of the following formula (I):

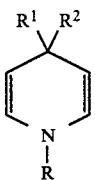
(I)

wherein
R is $-COR^3$, $R^4$, $-(CH_2)_nNR^5R^6$ or $-(CH_2)_nCOOR^7$;

$R^1$ is alkyl, phenyl, or phenyl substituted by 1 to 3 of alkyl, halo, trifluoromethyl, or nitro;

$R^2$ is alkyl, phenyl, or phenyl substituted by 1 to 3 of alkyl, halo, trifluoromethyl, or nitro, or $R^1$ and $R^2$ taken together may be cycloalkyl;

$R^3$ is phenyl, substituted phenyl, benzyl, substituted benzyl, diphenylmethyl, (substituted diphenyl)methyl, pyridyl, alkylamino, dialkylamino, N-pyrrolidino, N-piperidino, N-morpholino, dialkylaminoalkyl, or phenylamino, wherein the substitution on said substituted phenyl, substituted benzyl and each ring of said (substituted diphenyl)methyl is independently 1 to 3 of alkyl, halo, alkoxy, trifluoromethyl and nitro;

$R^4$ is thiazolyl, oxazolyl or such thiazolyl or oxazolyl substituted with alkyl, phenyl or phenyl which is itself substituted with 1 to 3 of alkyl, halo, alkoxy, trifluoromethyl or nitro;

$R^5$ is alkyl;

$R^6$ is alkyl or $R^5$ and $R^6$ together with the nitrogen atom to which they are attached define an N-Y ring of the following formula:

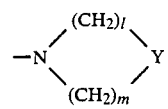

wherein
Y is $-CH_2-$, an oxygen atom or an $NR^8$ group;
$R^7$ is alkyl or benzyl;
$R^8$ is alkyl or phenyl;
l is 1,2, or 3;
m is 1,2, or 3;
l+m is 3,4, or 5;
n is 1,2,3,4,5 or 6; and,
the pharmaceutically acceptable acid addition salts thereof, with the proviso that when $R^3$ is phenyl, $R^1$ and $R^2$ cannot both be methyl.

In particular, $R^1$ and $R^2$ are independently alkyl of about 1 to 6 carbons such as methyl, ethyl, propyl, butyl, tert-butyl, sec-butyl, iso-butyl, pentyl, or hexyl; phenyl; or phenyl substituted with 1 to 3 groups independently selected from alkyl of about 1 to 4 carbons such as methyl, ethyl, or tert-butyl, halo such as fluoro, chloro, bromo or iodo, trifluoromethyl and nitro. Also, $R^1$ and $R^2$ together may be cycloalkyl of about 5 to 7 carbons such as spirocyclopentyl or spirocycloheptyl;

$R^3$ is phenyl; phenyl substituted with 1 to 3 substituents independently selected from alkyl of about 1 to 4 carbons, such as methyl, ethyl, propyl, 2-propyl, n-butyl, sec-butyl, tert-butyl, halo such as fluoro, chloro, bromo or iodo, alkoxy of about 1 to 4 carbons such as methoxy, ethoxy, n-propoxy, n-butoxy, or tert-butoxy, trifluoromethyl, or nitro; benzyl; benzyl substituted on the phenyl ring with 1 to 3 substituents independently selected from alkyl of about 1 to 4 carbons such as methyl, ethyl, or sec-butyl, halo such as fluoro, chloro bromo or iodo, alkoxy of about 1 to 4 carbons such as methoxy, ethoxy, or tert-butoxy, trifluoromethyl, or nitro; diphenylmethyl; diphenylmethyl substituted on one or both phenyl rings with 1 to 3 substituents independently selected from alkyl of about 1 to 4 carbons such as methyl, ethyl, n-propyl, or tert-butyl, halo such as fluoro, chloro, bromo or iodo, alkoxy of about 1 to 4 carbons such as methoxy, ethoxy, n-propoxy, or sec-butoxy, trifluoromethyl, or nitro; pyridyl such as 2-, 3- or 4-pyridyl; alkylamino, e.g. of about 1 to 4 carbons such as methylamino, ethylamino, n-propylamino, or n-butylamino; dialkylamino, e.g. of about 1 to 6 carbons in each alkyl moiety such as dimethylamino, diethylamino, methylethylamino, methyl-n-butylamino, or n-propyl-n-butylamino; N-pyrrolidino; N-piperidino; N-morpholino; dialkylaminoalkyl, e.g. of about 1 to 4 carbons in each alkyl moiety such as dimethylaminomethyl, dimethylaminoethyl, diethylaminoethyl, or di-n-propylaminobutyl; or, phenylamino;

$R^4$ is thiazolyl, e.g. 2-, 4- or 5-thiazolyl; such thiazolyl substituted with alkyl of about 1 to 4 carbons such as methyl or n-butyl, phenyl or phenyl substituted with 1 to 3 groups independently selected from alkyl of about 1 to 4 carbons, such as methyl or ethyl, halo such as fluoro, chloro, bromo or iodo, alkoxy of about 1 to 4 carbons such as methoxy, ethoxy, or tert-butoxy, trifluoromethyl, or nitro; oxazolyl, e.g. 2-, 4- or 5-oxazolyl; such oxazolyl substituted with alkyl of about 1 to 4 carbons such as methyl or t-butyl, phenyl, or phenyl substituted with 1 to 3 groups independently selected from alkyl of about 1 to 4 carbons, such as methyl or ethyl, halo such as fluoro, chloro, or bromo, alkoxy of about 1 to 4 carbons such as methoxy, ethoxy, or tert-butoxy, trifluoromethyl, or nitro.

$R^5$ is alkyl, e.g. of about 1 to 4 carbons such as methyl, ethyl, n-propyl, 2-propyl, or tert-butyl.

$R^6$ is alkyl, e.g. of about 1 to 4 carbons such as methyl, ethyl, n-propyl, or n-butyl.

$R^5$ and $R^6$ may together with the nitrogen atom to which they are attached define the above N-Y ring wherein Y is —$CH_2$—, an oxygen atom or an —$NR^8$ group, such as pyrrolidine ring, a morpholine ring or an N-substituted piperazine ring.

$R^7$ is alkyl, e.g. of about 1 to 4 carbons such as methyl, ethyl, n-propyl, 2-propyl, n-butyl, sec-butyl, iso-butyl, tert-butyl or benzyl.

$R^8$ is alkyl, e.g. of about 1 to 4 carbons such as methyl, ethyl, n-propyl, or t-butyl, or phenyl.

The pharmaceutically acceptable acid addition salts of the compounds of formula (I) include those of a mineral or organic acid such as hydrochloric, hydrobromic, hydroiodic, sulfuric, phosphoric, fumaric, maleic, cyclohexylsulfamic, citric, lactic, methanesulfonic, and similar acids.

Compounds of formula (I) may exist in various isomeric forms, e.g., in view of an asymmetric carbon. It is understood that the present invention includes all such individual isomers and their racemates. Also within the scope of the invention are compounds of the invention in the form of hydrates and other solvate forms.

Particular compounds of the invention may be defined as those of formula (I) having one or more of the following definitions: $R^1$ is alkyl, particularly methyl; $R^2$ is alkyl, particularly methyl; $R^3$ is phenyl (provided both $R^1$ and $R^2$ are not methyl), benzyl, diphenylmethyl, alkylamino, particularly methylamino, dialkylamino, alkylamino, particularly methylamino, dialkylamino, particularly dimethylamino, phenylamino, and pyridino, particularly 3-pyridino; R is —$(CH_2)_nNR^5R^6$ or —$(CH_2)_nCOOR^7$; $R^5$ is alkyl, particularly methyl, and $R^6$ is alkyl, particularly methyl or $R^5$ and $R^6$ together with the nitrogen atom to which they are attached define a morpholine ring or a piperazine ring substituted in the 4-position by methyl; $R^7$ is alkyl, particularly methyl; $R^8$ is alkyl, particularly methyl; l is the integer one, two or three; m is the integer one, two or three; and, the sum of l+m is the integer three, four or five.

Specific compounds of formula (I) of this invention are the following:

1,4-dihydro-1-[(3,4-dimethoxyphenyl)acetyl]4,4-dimethylpyridine;
1-diphenylacetyl-1,4-dihydro-4,4-dimethylpyridine;
1-benzoyl-1,4-dihydro-4,4-diphenylpyridine;
N,4,5-trimethyl-1(4H)-pyridinecarboxamide;
1,4-dihydro-N-methyl-4,4-diphenyl-1-pyridinecarboxamide;
1,4-dihydro-N,N,4,4-tetramethyl-1-pyridineethanamine;
1,4-dihydro-N,N-dimethyl-4,4-diphenyl-1-pyridineethanamine;
methyl 1,4-dihydro-4,4-dimethyl-1-pyridinebutanoate;
methyl 1,4-dihydro-4,4-dimethyl-1-pyridinepentanoate;
methyl 1,4-dihydro-4,4-bis-(4-methoxyphenyl)-1-pyridinebutanoate
methyl 1,4-dihydro-4,4-dimethyl-1-pyridinepropanoate;
1,4-dihydro-4,4-dimethyl-1-(3-pyridinecarbonyl)pyridine;
1-[(dimethylamino)acetyl]-1,4-dihydro-4,4-dimethylpyridine;
1-[(dimethylamino)acetyl]-1,4-dihydro-4,4-diphenylpyridine;
1,4-dihydro-4,4-dimethyl-N-phenyl-1-pyridinecarboxamide; and,
1,4-dihdro-4,4-dimethyl-1-(4-methyl-2-thiazolyl)pyridine.

As used throughout this specification, the term "alkyl" or "alkoxy" is meant to include all straight or branched chain groups within the carbon limits specified. The term "halo" comprises fluoro, chloro, bromo, or iodo.

Compounds of formula (I) may be prepared according to the following Reaction Scheme A wherein each of $R^1$, $R^2$, $R^3$, $R^4$, $R^5$, $R^6$ and $R^7$ are as defined for formula (I):

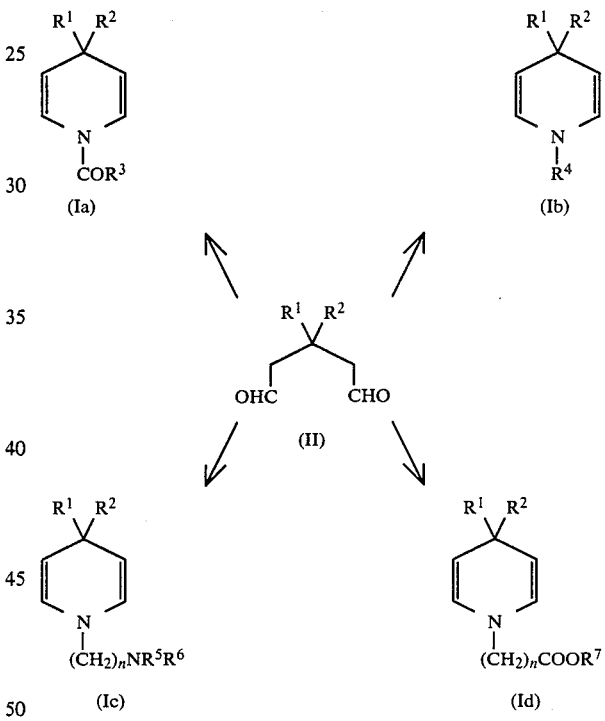

The 1,4,4-trisubstituted dihydropyridines of formulae (Ia), (Ib), (Ic) and (Id) above may be prepared by reaction of an appropriately substituted glutaraldehyde of the formula (II) with an amide or urea of the formula $H_2NCOR^3$, a 2-amino thiazoline or 2-amino oxazoline, a diamine of the formula $H_2N(CH_2)_nNR^5R^6$ or an aminoester of the formula $H_2N(CH_2)_nCOOR^7$, respectively.

To prepare (Ia) compounds, an appropriately substituted glutaraldehyde of the general formula (II) is combined with about one equivalent of an amide or urea of formula $H_2NCOR^3$ in a non-polar aprotic solvent such as benzene, toluene, or THF in the presence of an acid catalyst such as para-toluenesulfonic acid or trifluoroacetic acid. The reaction mixture is heated under an inert atmosphere such as nitrogen or argon and the water formed as a result of the condensation reaction is removed by azeotropic distillation. About two molar equivalents of magnesium sulfate added to the reaction mixture during the heating step in some cases helps to facilitate the reaction. The resulting 1,4,4-trisubstituted dihydropyridine of formula (Ia) is isolated and purified by techniques known to those skilled in the art of organic synthesis such as crystallization, trituration or chromatography.

To prepare (Ib) compounds, wherein $R^4$ is thiazolyl, substituted thiazolyl, oxazolyl, or substituted oxazolyl, an appropriately substituted glutaraldehyde of formula (II) is reacted with a 2-amino thiazole or a 2-amino oxazole in a solvent in the presence of an acid catalyst. In more detail, an appropriately substituted glutaraldehyde of formula (II) is combined with about one equivalent of an appropriately substituted 2-amino thiazole or 2-amino oxazole in an aprotic solvent such as benzene or toluene. The reaction mixture is heated for a period of about 16-21 hr at a temperature of about 80° C. in an inert atmosphere such as nitrogen or argon. Water is removed from the condensation reaction by azeotropic distillation. The addition of a catalytic amount of para-toluenesulfonic acid will facilitate this reaction. The product 1,4,4-trisubstituted dihydropyridine of formula (Ib) is isolated and purified by standard techniques.

To prepare (Ic) compounds, an appropriately substituted glutaraldehyde of the general formula (II) is combined with about one equivalent of an amine of formula $H_2N(CH_2)_nNR^5R^6$ in a non-polar aprotic solvent such as benzene or toluene. The reaction mixture is heated for a period of about 2 to 16 hours at a temperature of about 70° C. to 120° C., the refluxing temperature of the solvent being a convenient heating temperature, in an inert atmosphere such as nitrogen or argon to remove azeotroped water formed as a result of the condensation reaction. The resulting 1,4,4-trisubstituted dihydropyridine of formula (Ic) may then be isolated and purified by standard techniques.

To prepare (Id) compounds, an appropriately substituted glutaraldehyde of formula (II) is combined with about one equivalent of an amino ester hydrochloride of the amine $H_2N(CH_2)_nCOOR^7$ in an aprotic solvent such as chloroform and heated at a temperature of about 70° C. to 120° C. under an inert atmosphere such as nitrogen or argon for a period of about 16-21 hr in the presence of a water scavenger such as molecular sieves and about one equivalent of a strong base such as triethylamine. The product 1,4,4-trisubstituted dihydropyridine of formula (Id) is then isolated and purified by standard methods.

Glutaraldehydes of formula (II), amides, and ureas of formula $H_2NCOR^3$, 2-amino thiazoles, 2-amino oxazoles and amines and amino esters of formulae $H_2N(CH_2)_nNR^5R^6$ and $H_2N(CH_2)_nCOOR^7$ used as starting materials in Reaction Scheme A are commercially available, may be prepared by methods described herein or in the literature, or may be prepared by analogous methods thereto.

The compounds of formula (I) of this invention, including that where $R^3$=phenyl and $R^1$ and $R^2$=$CH_3$ are effective in lowering the blood pressure in mammals in need thereof, e.g., in humans, and are thus useful in the treatment of hypertension as evidenced by the Spontaneously Hypertensive Rat (SHR) test described below.

SPONTANEOUS HYPERTENSIVE RAT (SHR)

In this test, the arterial pressure of adult spontaneously hypertensive rats (Charles River) is monitored directly via an aortic cannula. The SH rats are anesthetized with an inhalation anesthetic (ether). The left carotid artery is isolated and cannulated. The top of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. The test compounds are administered to at least 3 rats at doses selected in the range of 0.1 to 100 mg/kg of body weight by intraperitoneal (i.p) or oral (p.o.) routes of administration. The arterial pressure and heart rate are monitored for a minimum of 24 hours. A test compound is considered to be active as an antihypertensive agent if the mean arterial pressure (MAP) indicates a fall of $\geq 15$ mm of Hg. Each animal serves as its own control.

The results of this test for compounds of formula (I), expressed as "Max Fall BP" (Maximum Fall in Mean Arterial Pressure) are shown in Table I.

TABLE I

| Ex. No. | R | $R^1$ | $R^2$ | Max Fall BP$^a$ (dose$^b$) |
|---|---|---|---|---|
| 1 | $-\overset{O}{\underset{\|\|}{C}}-Ph$ | $CH_3$ | $CH_3$ | 27 (100) |
| $2^b$ | $-\overset{O}{\underset{\|\|}{C}}-CH_2-3,4-diOMePh$ | $CH_3$ | $CH_3$ | 22 (30 ip) |
| $3^b$ | $-\overset{O}{\underset{\|\|}{C}}-CHPh_2$ | $CH_3$ | $CH_3$ | 24 (30 ip) |
| $4^b$ | $-\overset{O}{\underset{\|\|}{C}}-Ph$ | Ph | Ph | 15 (100) |
| 5 | $-\overset{O}{\underset{\|\|}{C}}NHCH_3$ | $CH_3$ | $CH_3$ | 41 (100) |
| 6 | $-\overset{O}{\underset{\|\|}{C}}NHCH_3$ | Ph | Ph | 15 (100) |
| 7 | $-(CH_2)_2N(CH_3)_2$ | $CH_3$ | $CH_3$ | 35 (30 ip) |
| 8 | $-(CH_2)_2N(CH_3)_2$ | Ph | Ph | 31 (30 ip) |
| $9^b$ | $-(CH_2)_3COOCH_3$ | $CH_3$ | $CH_3$ | 41 (100) |
| $10^b$ | $-(CH_2)_4COOCH_3$ | $CH_3$ | $CH_3$ | 59 (30 ip) |
| $11^c$ | $-(CH_2)_3COOCH_3$ | 4-OMePh | 4-OMePh | 24 (100) |
| $12^b$ | $-(CH_2)_2COOCH_3$ | $CH_3$ | $CH_3$ | 28 (100) |
| 13 | $-\overset{O}{\underset{\|\|}{C}}-3\text{-pyridinyl}$ | $CH_3$ | $CH_3$ | 25 (100) |
| 14 | $-\overset{O}{\underset{\|\|}{C}}-CH_2N(CH_3)_2$ | $CH_3$ | $CH_3$ | 39 (100) |
| 15 | $-\overset{O}{\underset{\|\|}{C}}-CH_2N(CH_3)_2$ | Ph | Ph | 31 (30 ip) |
| 16 | $-\overset{O}{\underset{\|\|}{C}}-NHPh$ | $CH_3$ | $CH_3$ | 27 (30 ip) |

TABLE I-continued

| Ex. No. | R | $R^1$ | $R^2$ | Max Fall $BP^a$ (dose$^b$) |
|---|---|---|---|---|
| 17 | (structure: 2-thiazolyl with CH₃ substituent) | CH₃ | CH₃ | 21 (100) |

$^a$in mm of Hg
$^b$in mg/kg of bodyweight, p.o., unless otherwise noted.

For the treatment of hypertension, compounds of the present invention of the formula (I) may be administered orally or parenterally in a pharmaceutical composition comprising about 50 to 500 mg of one or more of the dihydropyridine compounds per day for an average adult human depending on the activity of the particular compound chosen. The dosage may be divided into 1 to 4 unit dosage forms per day. While the therapeutic methods of the invention are most useful for human subjects in need of alleviation of hypertension, the compounds may be administered to other mammals at comparable dosages per weight of the subject.

Pharmaceutical compositions containing the 1,4,4-trisubstituted dihydropyridine compounds of the present invention of formula (I), or an acid addition salt thereof as the active ingredient may be prepared by intimately mixing the dihydropyridine compound with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, including liquid carriers such as water, glycols, oils, alcohols and the like for oral liquid preparations such as suspensions, elixers and solutions; and solid carriers such as starches, sugars, kaolin, calcium stearate, ethyl cellulose, etc., including materials which function as lubricants, binders, disintegrating agents and the like for powders, capsules and tablets. Because of their ease in administration, tablets and capsules represent the most advantageous oral dosage form. These compositions employ solid pharmaceutical carriers such as the aforementioned starches, sugars, kaolin and the like, generally with a lubricant such as calcium stearate. It is especially advantageous to formulate the aforementioned pharmaceutical compositions in dosage unit form for ease of administration and uniformity of dosage. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonful, tablespoonful and the like, and segregated multiples thereof.

In the following examples, the following abbreviations are used: bp (boiling point); mp (melting point); g (grams); ml (milliliters); M (molar) THF (tetrahydrofuran); MeOH (methanol); MEK (methylethylketone); Ph (phenyl); Me (methyl); DIBAH (diisobutyl aluminum hydride); mmoles (millimoles); mg (milligrams); mm (millimeters); and C,H,N, etc. (the chemical symbols for the elements). Unless otherwise indicated, all temperatures are reported in degrees centigrade (°C.) and all pressures in mm of mercury.

EXAMPLE 1

1-Benzoyl-1,4-dihydro-4,4-dimethylpyridine

The title compound was prepared as by the method of Fraenkel, et. al., Tetrahedron Letters, 1407–1410(1978). A 91% yield of crude product was isolated as a yellow oil. The desired compound was purified by silica gel column chromatography using 50 g of CC-7 silica per gram of crude product using a 2% ethyl acetate/hexane solution as the eluant. The eluate was evaporated in vacuo to yield the title compound as a clear oil which crystallized upon standing, mp 57°–59° C.

Elemental Analysis: Calc'd for $C_{14}H_{15}NO$: C, 78.84; H, 7.09; N, 6.57. Found: C, 78.84; H, 7.11; N, 6.57.

EXAMPLE 2

1,4-Dihydro-1-[(3,4-dimethoxyphenyl)acetyl]-4,4-dimethyl-pyridine a. (3,4-Dimethoxyphenyl)acetamide To a solution of 35.31 g (0.18 mole) of (3,4-dimethoxyphenyl)acetic acid in 345 ml of dry toluene and 34.5 ml of dry DMF at 0° C. under argon was added 16.8 ml (0.19 mole) of freshly distilled oxalyl chloride over 40 minutes. The reaction was stirred an additional 35 minutes at 0° C. and then at room temperature for 17 hours. The reaction mixture was again cooled to 0° C. and gaseous ammonia slowly bubbled through it for 1 hour. The reaction mixture was warmed to room temperature and stirred for 4 hours after which the solid was filtered off and partitioned between chloroform and water. The organic phase was washed with brine, dried over anhydrous magnesium sulfate, filtered and evaporated in vacuo giving 20.84 g of the title compound as an off-white solid, mp 142°–144° C.

b. 1,4-Dihydro-1-[(3,4-dimethoxyphenyl)acetyl]-4,4-dimethylpyridine

In 180 ml of benzene 4.88 g (0.025 mole) of (3,4-dimethoxyphenyl)acetamide (the compound of Example 2a) was combined with 3.20 g (0.025 mole) of 3,3-dimethylglutaraldehyde, prepared by the method of G.Fraenkel, et.al., J. Org. Chem., 44(14), 2522-29(1979), and 0.13 g (0.7 mmole) para-toluenesulfonic acid monohydrate under nitrogen. The reaction mixture was warmed to reflux and water was azeotroped off via a Dean-Stark trap. After 3 hours the benzene was evaporated in vacuo giving 7.74 g of crude product. The crude product was purified by silica gel column chromatography on 375 g of CC-7 silica gel eluting with a 15% ethyl acetate/hexane solution. The eluate was evaporated in vacuo to yield a white solid residue which was the title compound; 4.68 g, mp 86°–89.5° C.

Elemental Analysis: Calc'd for $C_{17}H_{21}NO_3$: C, 71.06; H, 7.37; N, 4.87. Found: C, 71.03; H, 7.38; N, 4.87.

EXAMPLE 3

1-Diphenylacetyl-1,4-dihydro-4,4-dimethylpyridine a. 2,2-Diphenylacetamide

The title compound was prepared using the method of Example 2a substituting an equivalent quantity of diphenylacetic acid for (3,4-dimethoxyphenyl)acetic acid as the starting acid. The title compound was isolated as a white solid, mp 168°–171° C.

b. 1-Diphenylacetyl-1,4-dihydro-4,4-dimethylpyridine

The title compound was prepared using the method of Example 2b after substituting an equivalent quantity of 2,2-diphenylacetamide (the compound of Example 3a) for (3,4-dimethoxyphenyl)acetamide as the starting amide. The crude product was crystallized from isopropanol to obtain the title compound as a white solid, mp 116°–118° C.

Elemental Analysis: Calc'd for $C_{21}H_{21}NO$: C, 83.13; H, 6.98; N, 4.62. Found: C, 83.12; H, 6.98; N, 4.62.

EXAMPLE 4

1-Benzoyl-1,4-dihydro-4,4-diphenylpyridine a. 3,3-Diphenylglutaraldehyde

To a rapidly stirring solution of 14.24 g(0.04 mole) of diethyl 3,3-diphenylglutarate, prepared by the method of H. Ivanov and I. Anghelova, Comptes Rendus Acan. Bul. Sci., 18 (6), 529-32(1965), in 320ml of dry toluene at −78° C. under argon was added 61.12 ml (0.11 mole) of 1.86M DIBAL in toluene solution (Aldrich) over a period of 4 minutes. After 40 minutes, 40 ml of methanol was added over 4 minutes to the −78° C., stirring reaction mixture. After an additional 5 minutes of stirring, 80 ml of water was added over a 5 minute period while keeping the temperature of the reaction at −78° C. The reaction mixture was allowed to warm to room temperature and was stirred an addititional hour. The reaction mixture was filtered and the precipitated salts washed with 300 ml of warmed toluene (100° C.) and then 300 ml of boiling methylene chloride. The organic phase of the filtrate was separated, dried over anhydrous magnesium sulfate, filtered, and evaporated in vacuo giving a clear oil. The oil was used in the next step without further purification.

b. 1-Benzoyl-1,4-dihydro-4,4-diphenylpyridine

The title compound was prepared using the method of Example 2b after substituting equivalent quantities of benzamide for (3,4-dimethoxyphenyl)acetamide and 3,3-diphenylglutaraldehyde (the compound of Example 4a) for 3,3-dimethylglutaraldehyde as starting materials. The crude product was purified by silica gel flash chromatography eluting with a 7% ethyl acetate/hexane solution. The eluate was evaporated in vacuo to yield a clear oil which, after triturating with methanol, gave the title compound as a white solid, mp 91°–93° C.

Elemental Analysis: Calc'd for $C_{24}H_{19}NO$: C, 85.43; H, 5.68; N, 4.15.

Found: C, 85.34; H, 6.02; N, 3.98.

EXAMPLE 5

N,4,4-Trimethyl-1(4H)-pyridinecarboxamide

The title compound was prepared using the method of Example 2b after substituting an equivalent amount of methylurea for (3,4-dimethoxyphenyl)acetamide as a starting material and diluting the solution three-fold with benzene. The crude product was purified by silica gel flash chromatography eluting with a 25% ethyl acetate/hexane solution. The eluate was evaporated in vacuo to yield the title compound as a white solid, mp 129°–131° C.

Elemental Analysis: Calc'd for $C_9H_{14}N_2O$: C, 65.03; H, 8.49; N, 16.85. Found: C, 64.88; H, 8.50; N, 16.83.

EXAMPLE 6

1,4-Dihydro-N-methyl-4,4-diphenyl-1-pyridinecarboxamide

The title compound was prepared using the method of Example 2b after substituting an equivalent amount of 3,3-diphenylglutaraldehyde (the compound of Example 4a) for 3,3-dimethylglutaraldehyde, substituting methylurea for (3,4-dimethoxyphenyl)acetamide, and diluting the solution six fold with benzene. A 7.06 g sample of the crude product was partially purified by silica gel flash chromatography eluting with a 30% ethyl acetate/hexane solution. The eluate was evaporated in vacuo to obtain 3.66 g of semi-pure product. The 3.66 g sample was triturated in 20 ml of ice cold acetonitrile, filtered, and dried overnight under high vacuum at room temperature to yield the title compound as a white solid, mp 180°–182° C.

Elemental Analysis: Calc'd for $C_{19}H_{18}N_2O$: C, 78.59; H, 6.25; N, 9.65. Found: C, 78.62; H, 6.28; N, 9.63.

EXAMPLE 7

1,4-Dihydro-N,N,4,4-tetramethyl-1-pyridineethanamine

In 100 ml of benzene 3.30 ml (0.03 mole) of N,N-dimethylethylenediamine was combined with 3.84 g (0.03 mole) of 3,3-dimethylglutaraldehyde under nitrogen. The reaction mixture was warmed to reflux and water azeotroped off via a Dean-Stark trap. After 15 hours the benzene was evaporated in vacuo giving 5.76 g of crude product as a brown liquid. The crude product was distilled to yield 2.41 g of the title compound as a clear liquid, bp 60° C./0.2 mm Hg.

Elemental Analysis: Calc'd for $C_{11}H_{20}N_2$: C, 73.28; H, 11.18; N, 15.54. Found: C, 73.10; H, 11.18; N, 15.47.

EXAMPLE 8

1,4-Dihydro-N,N-dimethyl-4,4-diphenyl-1-pyridineethanamine

The title compound was prepared using the method of Example 7 after substituting an equivalent amount of 3,3-diphenylglutaraldehyde (the compound of Example 4a) for 3,3-dimethylglutaraldehyde as a starting material. The crude product was purified by silica gel flash chromatography eluting with a 1.5% ethanol/methylene chloride solution. The eluate was evaporated in vacuo to yield the title compound as a clear oil which crystallized as a white solid upon standing, mp 60°–63° C.

Elemental Analysis: Calc'd for $C_{21}H_{24}N_2$: C, 82.85; H, 7.95; N, 9.20. Found: C, 82.74; H, 7.99; N, 9.09.

EXAMPLE 9

Methyl 1,4-dihydro-4,4-dimethyl-1-pyridinebutanoate a. Methyl 4-Aminobutanoate Hydrochloride Anhydrous HCl was slowly bubbled into a heterogeneous mixture of 20.64 g (0.2 mole) of 4-aminobutyric acid in 200 ml of methanol at room temperature. After adding the HCl for about 5 minutes the reaction mixture warmed to a gentle reflux at which time it was submerged into a 0° C. ice bath. HCl addition was continued for an additional 5 minutes after the reaction mixture was cooled. The reaction mixture was then placed under nitrogen and refluxed for 17 hours. The solvent was evaporated in vacuo giving 30.70 g of a white solid, mp 110°14 115° C. The title compound was used in the next step without further purification.

b. Methyl 1,4-dihydro-4,4-dimethyl-1-pyridinebutanoate

Under nitrogen, 5.89 g (0.046 mole) of 3,3-dimethylglutaraldehyde, 7.03 g (0.0457 mole) of methyl 4-aminobutanoate hydrochloride (the compound of Example 9a), and 9 g of 5A molecular sieves were combined in 425 ml of chloroform at room temperature. 7.0 ml (0.05 mole) of triethylamine were added to the reaction mixture before it was warmed to reflux. After 21 hours the reaction mixture was cooled to room temperature, filtered, and the filtrate evaporated in vacuo. The residue was suspended in about 300 ml of ethyl ether and filtered. The filtrate was evaporated in vacuo to yield 8.56 g of crude product. The crude product was distilled to yield 2.5 g of the title compound as a clear liquid, bp 95° C./0.2 mm Hg.

Elemental Analysis: Calc'd for $C_{12}H_{19}NO_2$: C., 68.87; H, 9.15; N, 6.69. Found: C, 68.72; H, 9.17; N, 6.72.

EXAMPLE 10

Methyl 1,4-dihydro-4,4-dimethyl-1-pyridinepentanoate a. Methyl 5-aminopentanoate Hydrochloride The title compound was prepared using the method of Example 9a after substituting an equivalent amount of 5-aminovaleric acid for 4-aminobutyric acid as a starting material. The title compound was isolated as a white solid, mp 139°–142° C.

b. Methyl 1,4-dihydro-4,4-dimethyl-1-pyridinepentanoate

The title compound was prepared using the method of Example 9b after substituting an equivalent amount of methyl 5-aminopentanoate hydrochloride (the compound of Example 10a) for methyl 4-aminobutanoate hydrochloride as a starting material. A 9.8 g sample of the crude product was partially purified by silica gel flash chromatography on a 400 ml column, eluting with a 5% ethyl acetate/hexane solution. The eluate was evaporated in vacuo and the 4.10 g liquid residue vacuum distilled to yield 3.35 g of the title compound as a clear liquid, b.p. 82°–90° C./0.1 mm Hg.

Elemental Analysis: Calc'd for $C_{13}H_{21}NO_2$: C, 69.92; H, 9.48; N, 6.27. Found: C, 70.00; H, 9.50; N, 6.27.

EXAMPLE 11

Methyl 1,4-dihydro-4,4-bis-(4-methoxyphenyl)-1-pyridine-butanoate a. Diethyl 3,3-(4-methoxyphenyl)glutarate In 640 mls of ethanol, 172 g (0.5 mole) of 3,3-(4-methoxyphenyl)glutaric acid prepared by the method of K. D. Deodhar, et al, Indian Journal of Chemistry, Vol. 20B, 572–574 (1981) was combined with 6 ml of concentrated sulfuric acid under argon and the solution was warmed to reflux. After 3 days the solvent was evaporated in vacuo. The resulting residue was dissolved in 300 ml of ethyl ether and extracted with 400 ml of water, twice with 200 ml of saturated sodium bicarbonate, and finally with 200 ml of brine solution. The organic phase was dried over anhydrous magnesium sulfate, filtered and evaporated in vacuo to yield 157 g of the title compound as a yellow oil. The title compound was used in the next step without further purification.

b. 3,3-(4-methoxyphenyl)glutaraldehyde

The title compound was prepared using the method of Example 4a after substituting an equivalent amount of diethyl 3,3-(4-methoxyphenyl)glutarate (the compound of Example 11a) for diethyl 3,3-diphenylglutarate as a starting material. On the final work-up a crude yellow oil was recovered. The crude yellow oil was used in the next step without further purification.

c. Methyl 1,4-dihydro-4,4-bis-(4-methoxyphenyl)-1-pyridine-butanoate

The title compound was prepared using the method of Example 9b after substituting an equivalent amount of 3,3-(4-methoxyphenyl)glutaraldehyde (the compound of Example 11b) for 3,3-dimethylglutaraldehyde as a starting material. The crude reaction mixture was partially purified by silica gel flash chromatography eluting with a 20% ethyl acetate/hexane solution. The eluate was evaporated in vacuo and the resulting oil triturated twice with small amounts of methanol at −20° C. to give the title compound as a white solid, mp 36°–38° C.

Elemental Analysis: Calc'd for $C_{24}H_{27}NO_4$: C, 73.26; H, 6.92; N, 3.56. Found: C, 73.17; H, 6.92; N, 3.51.

EXAMPLE 12

Methyl 1,4-dihydro-4,4-dimethyl-1-pyridinepropanoate a. Methyl 3-aminopropanoate hydrochloride The title compound was prepared using the method of Example 9a after substituting an equivalent amount of 3-aminopropionic acid for 4-aminobutyric acid as a starting material. The title compound was isolated as a white solid, mp 87°–93° C.

b. Methyl 1,4-dihydro-4,4-diemethyl-1-pyridinepropanoate

The title compound was prepared using the method of Example 9b after substituting an equivalent amount of methyl 3-aminopropanoate hydrochloride (the compound of Example 12a) for methyl 4-aminobutanoate hydrochloride as a starting material. The crude product, a yellow liquid, was distilled to yield the title compound as a colorless liquid, bp 60°–62° C./0.05 mm Hg.

Elemental Analysis: Calc'd for $C_{11}H_{17}NO_2$: C, 67.66; H, 8.78; N, 7.17. Found: C, 67.66; H, 8.84; N, 7.14.

EXAMPLE 13

1,4-Dihydro-4,4-dimethyl-1-(3-pyridinylcarbonyl)pyridine Ethanedioate Hydrate (2:2:1)

In 500 ml of benzene, 6.41 g (0.05 mole) of 3,3-dimethylglutaraldehyde, 6.11 g (0.05 mole) of nicotinamide, 4.24 ml (0.55 mole) of trifluoroacetic acid, and 12.04 g (0.10 mole) of anhydrous magnesium sulfate were combined under nitrogen and warmed to reflux. After 6 days the reaction mixture was cooled, filtered, and the filtrate evaporated in vacuo to give 11.45 g of a brown oil. This brown oil was partially purified via liquid chromatography with a Water Prep 500 GLC which was dual loaded with 2 silica gel columns using a 40% ethyl acetate/hexane solution for elution. The fractions containing the desired product were combined and evaporated in vacuo to give 6.36 g of a yellow oil. This material was dissolved in 250 ml of chloroform and extracted with 100 ml of 15% NaOH and then with 100 ml of water. The organic phase was dried over anhydrous magnesium sulfate, filtered, and evaporated in vacuo to yield 4.45 g of a light yellow oil. The yellow oil was dissolved in 10 ml of ethyl ether and combined with 2.62 g (0.021 mole) of oxalic acid dissolved in 10 ml of ethanol. This solution was diluted with 10 ml of hexane and the resulting solid filtered to yield 4.25 g of yellow tinted crystals. The yellow tinted crystals were dissolved in 95 ml of a 1:3 ethanol/ethyl ether solution. This solution was diluted with 175 ml of hexane and the resulting precipitate filtered, rinsed with hexane, and dried in vacuo overnight at room temperature to yield 3.62 g of the title compound as a white solid, mp 120°-122° C.

Elemental Analysis: Calc'd for $C_{13}H_{14}N_2O \cdot C_2H_2O_4$ 0.5 $H_2O$: C, 57.47; H, 5.47; N, 8.94. Found: C, 57.25; H, 5.50; N, 8.89.

EXAMPLE 14

1-[(Dimethylamino)acetyl]-1,4-dihydro-4,4-dimethyl-pyridine-(Z)-2-Butenediote

In 115 ml of benzene, 2.56 g (0.02 mole) of 3,3-dimethylglutaraldehyde was combined with 2.04 g (0.02 mole) of 2-(dimethylamino)acetamide and 4.20 g (0.022 mole) of p-toluenesulfonic acid monohydrate under nitrogen. The reaction mixture was warmed to reflux and water azeotroped off via a Dean-Stark trap. After 3 hours the reaction mixture was allowed to cool to room temperature and was then extracted with 15% NaOH. The organic phase was then extracted with brine, dried over anhdrous magnesium sulfate, filtered, and evaporated in vacuo to yield 2.79 g of a yellow oil. A 1.98 g sample of the yellow oil in 30 ml of ethyl ether was combined with 1.16 g (0.01 mole) of maleic acid dissolved in 10 ml of ethanol. The resulting precipitate was filtered, rinsed with a small amount of ether, and allowed to air dry to give 2.75 g of a white solid. The white solid was twice recrystallized from about 15 ml of acetonitrile, filtered, rinsed with about 3 ml of cold acetonitrile and then with ethyl ether. The resulting white solid was air dried to yield 1.48 g of the title compound, mp 179°-181° C.

Elemental Analysis: Calc'd for $C_{11}H_{18}N_2O \cdot C_4H_4O_4$: C, 58.05; H, 7.14; N, 9.03. Found: C, 57.98; H, 7.22; N, 9.05.

EXAMPLE 15

1-[(Dimethylamino)acetyl]-1,4-dihydro-4,4-diphenyl-pyridine Hydrochloride (1:1)

The title compound was prepared using the method of Example 14 after substituting an equivalent amount of 3,3-diphenylglutaraldehyde (the compound of Example 4a) for 3,3-dimethylglutaraldehyde, diluting the solution four fold with benzene, and refluxing the reaction mixture for 5 days rather than 3 hours. The purification procedure for the title compound varied from that of Example 14. After cooling the reaction mixture to room temperature, it was extracted with a dilute potassium carbonate solution which resulted in an emulsion. After filtering, the layers were easily separated and the organic phase was extracted with a 3N HCl solution half the volume of the organic phase. A darkish purple solid insoluble in either phase precipitated out during the extraction and was filtered. A 4.5 g sample of the purple solid was suspended in 60 ml of boiling methyl ethyl ketone, filtered, and rinsed with 20 ml more of MEK to give 2.87 g of a slightly purple tinted white solid. This sample was dissolved in about 35 ml of methanol, refluxed for about 10 minutes after adding activated charcoal powder, and then filtered. The methanol solution was diluted with ethyl ether until the solution became turbid. Upon scratching a white precipitate fell out of solution which was filtered and rinsed with a small amount of ethyl ether to give 1.78 g of the title compound as a white solid, mp 242°-244.5° C.

Elemental Analysis: Calc'd for $C_{21}H_{22}N_2O \cdot HCl$: C, 71.08; H, 6.53; N, 7.89. Found: C, 70.65; H, 6.52; N, 7.94.

EXAMPLE 16

1,4-Dihydro-4,4-dimethyl-N-phenyl-1-pyridinecarboxamide

A mixture of 4.57 g (0.036 mole) of 3,3-dimethylglutaraldehyde, 0.20 g (0.001 mole) of p-toluenesulfonic acid monohydrate and 8.64 g (0.072 mole) of anhydrous magnesium sulfate in 300 ml of dry THF was heated to reflux under nitrogen. 4.89 g (0.036 mole) of phenylurea in 125 ml of dry THF was added over a period of 1 hour. Refluxing was continued for an additional 40 minutes before the reaction mixture was filtered and the filtrate evaporated in vacuo to yield 8.23 g of a brown oil. The crude product was purified by silica gel column chromatography on 410 g of CC-7 silica gel eluting with a 7.5% ethyl acetate/hexane solution. The eluate was evaporated in vacuo to yield 4.74 g of the title compound, a white solid, mp 128°-130° C.

Elemental Analysis: Calc'd for $C_{14}H_{16}N_2O$: C, 73.66; H, 7.06; N, 12.27. Found: C, 73.63; H, 7.11; N, 12.29.

EXAMPLE 17

1,4-Dihydro-4,4-dimethyl-1-(4-methyl-2-thiazolyl)pyridine

In 170 ml of benzene, 4.45 1 g (0.035 mole) of 3,3-dimethylglutaraldehyde was combined with 3.96 (0.035 mole) of 2-amino-4-methylthiazole under nitrogen. The reaction mixture was brought to reflux and water azeotroped off via a Dean-Stark trap. After 21 hours 0.20 g (0.001 mole) of p-toluenesulfonic acid monohydrate was added to the reaction mixture and heating continued an additional 5 hours after which the solvent was evaporated in vacuo. The crude product was purified by silica gel flash chromatography eluting with a 1% ethyl acetate/hexane solution. The eluate was evaporated in vacuo to yield 2.67 g of the title compound as a clear liquid.

Elemental Analysis: Calc'd for $C_{11}H_{14}N_2S$: C, 64.04; H, 6.84; N, 13.58. Found: C, 64.02; H, 6.88; N, 13.55.

What is claimed is:

1. A 1,4,4-trisubstituted dihydropyridine compound of the following formula (I):

wherein

R is $—COR^3$, $—(CH_2)_nNR^5R^6$ or $—(CH_2)_nCOOR_7$;

$R^1$ is alkyl of 1 to 6 carbons, phenyl, or phenyl substituted by 1 to 3 of alkyl of 1 to 4 carbons, halo, trifluoromethyl, or nitro;

$R^2$ is alkyl of 1 to 6 carbons, phenyl, or phenyl substituted by 1 to 3 of alkyl of 1 to 4 carbons, halo, trifluoromethyl, or nitro;

$R^3$ is phenyl, substituted phenyl, benzyl, substituted benzyl, diphenylmethyl, (substituted diphenyl)methyl, alkylamino of 1 to 4 carbons, dialkylamino of 1 to 4 carbons in each alkyl moiety, dialkylaminoalkyl of 1 to 4 carbons in each alkyl moiety, or phenylamino, wherein the substitution on said substituted phenyl, substituted benzyl and each ring of said (substituted diphenyl)methyl is independently 1 to 3 of alkyl of 1 to 4 carbons, halo, alkoxy of 1 to 4 carbons, trifluoromethyl and nitro;

$R^5$ is alkyl of 1 to 4 carbons;

$R^6$ is alkyl of 1 to 4 carbons;

$R^7$ is alkyl of 1 to 4 carbons or benzyl;

n is one, two, three, four, five or six; and, a pharmaceutically acceptable acid addition salt thereof, with the provisos (i) that when $R^3$ is phenyl, both $R^1$ and $R^2$ are not methyl and (ii) that when $R^3$ is dimethylamino, both $R^1$ and $R^2$ are not methyl.

2. The dihydropyridine of claim 1,
wherein $R^1$ is alkyl of 1 to 6 carbons; phenyl; or phenyl substituted by 1 to 3 groups independently selected from alkyl of 1 to 4 carbons, alkoxy of 1 to 4 carbons, halo, trifluoromethyl, or nitro;

$R^2$ is alkyl of 1 to 6 carbons, phenyl, or phenyl substituted by 1 to 3 groups independently selected from alkyl of 1 to 4 carbons, alkoxy of 1 to 4 carbons, halo, trifluoromethyl, or nitro;

$R^3$ is phenyl; phenyl substituted with 1 to 3 substituents independently selected from alkyl of 1 to 4 carbons, halo, alkoxy of 1 to 4 carbons, trifluoromethyl, or nitro; benzyl; benzyl substituted on the phenyl ring with 1 to 3 substituents independently selected from alkyl of 1 to 4 carbons, halo, alkoxy of 1 to 4 carbons, trifluoromethyl, or nitro; diphenylmethyl; diphenylmethyl substituted on one or both phenyl rings with 1 to 3 substituents independently selected from alkyl of 1 to 4 carbons, halo, alkoxy of 1 to 4 carbons, trifluoromethyl, or nitro; alkylamino of 1 to 4 carbons; dialkylamino of 1 to 4 carbons in each alkyl moiety; dialkylaminoalkyl of 1 to 4 carbons in each alkyl moiety; or, phenylamino;

$R^5$ is alkyl of 1 to 4 carbons;

$R^6$ is alkyl of 1 to 4 carbons;

$R^7$ is alkyl of 1 to 4 carbons.

3. The dihydropyridine of claim 1, wherein both $R^1$ and $R^2$ are methyl.

4. The dihydropyridine of claim 1, wherein R is —$COR^3$.

5. The dihydropyridine of claim 1, wherein R is —$(CH_2)_n NR^5 R^6$.

6. The dihydropyridine of claim 1, wherein R is —$(CH_2)_n COOR^7$.

7. The dihydropyridine of claim 1, wherein $R^3$ is alkylamino, dialkylamino or dialkylaminoalkyl.

8. The dihydropyridine of claim 1 wherein R is —$(CH_2)_n NR^5 R^6$ and $R^5$ and $R^6$ are alkyl.

9. The dihydropyridine of claim 8, wherein R is —$CH_2 CH_2 N(CH_3)_2$.

10. The dihydropyridine of claim 1 selected from the group consisting of:

1,4-dihydro-1-[(3,4-dimethoxyphenyl)acetyl]-4,4-dimethylpyridine:

1-diphenylacetyl-1-1,4-dihydro-4,4-dimethylpyridine;

1-benzoyl-1,4-dihydro-4,4-diphenylpyridine;

N,4,4-trimethyl-1(4H)-pyridinecarboxamide;

1,4-dihydro-N-methyl-4,4-diphenyl-1-pyridinecarboxamide;

1,4-dihydro-N,N,4,4-tetramethyl-1-pyridineethanamine;

1,4-dihydro-N,N-dimethyl-4,4-diphenyl-1 pyridineethanamine;

methyl 1,4-dihydro-4,4-dimethyl-1-pyridinebutanoate;

methyl 1,4-dihydro-4,4-dimethyl-1-pyridinepentanoate;

methyl 1,4-dihydro-4,4-bis-(4-methoxyphenyl)-1-pyridinebutanoate;

methyl 1,4-dihydro-4,4-dimethyl-1-pyridinepropanoate;

1-[(dimethylamino)acetyl]-1,4-dihydro-4,4-dimethylpyridine;

1-[(dimethylamino)acetyl]-1,4-dihydro-4,4-diphenylpyridine; and 1,4-dihydro-4,4-dimethyl-N-phenyl-1-pyridinecarboxamide.

11. A pharmaceutical composition for treating hypertension comprising an effective anti-hypertensive amount of a 1,4,4-trisubstituted dihydropyridine of claim 1 in combination with a pharmaceutically acceptable diluent or carrier.

12. A method of treating hypertension which comprises administering to a mammal in need thereof, the pharmaceutical composition of claim 11.

13. The method of claim 12, wherein the mammal is a human.

* * * * *